March 28, 1944. W. E. LAMMERTS Plant Pat. 621
PEACH TREE
Filed Nov. 27, 1943
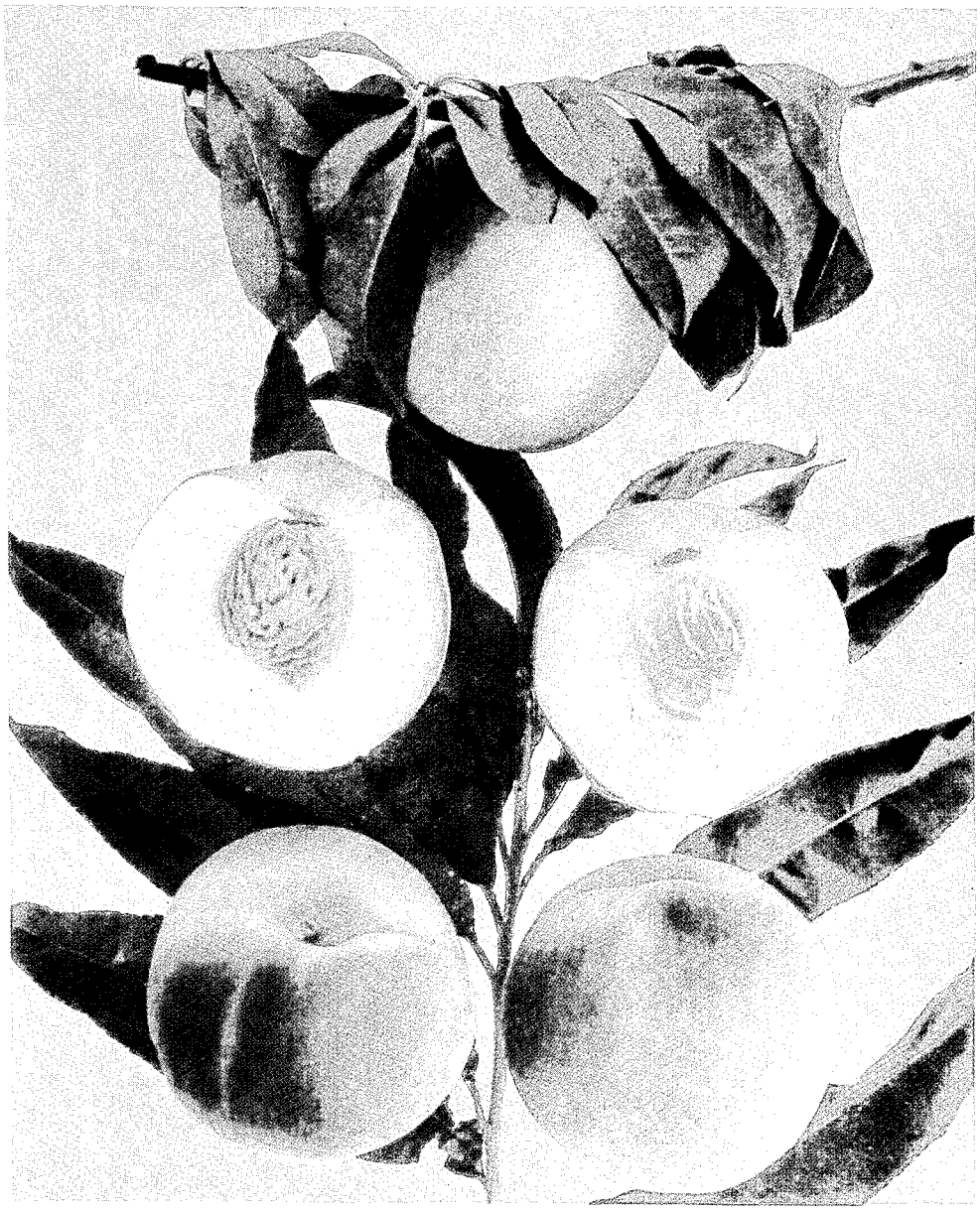
Inventor
Walter E. Lammerts
By Robb & Robb
Attorneys Patented Mar. 28, 1944

Plant Pat. 621

UNITED STATES PATENT OFFICE

621

PEACH TREE

Walter E. Lammerts, West Los Angeles, Calif., assignor to Armstrong Nurseries, Inc., Ontario, Calif., a corporation of California Application November 27, 1943, Serial No. 511,981

1 Claim. (Cl. 47—62)

The present invention relates to a new and distinct variety of peach tree, resulting from a cross of the two known varieties, the "Babcock," especially well known as a Southern California Peach, and the Stensgaard strain of "July Elberta."

The new variety is notably distinct, to begin with, because of the size which its fruit attains in the early period of ripening, which period is from a week to ten days earlier than the "Babcock." In respect to size, it averages about one-half inch larger in diameter than the "Babcock" with a relatively larger pit or stone, and in shape also it differs from the latter in that it has a typical, although slight, apical point.

In further comparison with the parent "Babcock" variety, the skin color of the fruit is more attractive, as shown in the accompanying drawing, because of the pattern in which the colors are laid in predominate streaks or stripes and blotches, and often the fruits will have white dotting in some of the more heavily colored areas. When allowed to hang on the tree until soft-ripe, the fruit will develop considerable pink and red coloring in the tender fibers, although when first ripe they are what are commonly known as white-fleshed.

This new peach further differs from the "Babcock" variety because of its full-bodied flavor and its excellent balance between sugar and acid, unusual in a peach of the early ripening characteristic.

In Southern California it has about the same amount of resistance to delayed dormancy as does the variety "Socala," a commercial yellow-fleshed peach much planted in this area and its ability to produce regular crops in this section, where often the winters are too mild for proper dormancy in many varieties, and to leaf out and to flower under such conditions, together with its habit of developing high flavor regardless of weather conditions preceding the ripening period, mark other very important points of distinction.

Asexual reproduction shows that these characteristics hold true through succeeding propagations.

The following is a detailed description of this new variety, color terminology being in accord with Robert F. Wilson Horticultural Colour Chart:

Seedling: Resulting from "Babcock" x Stensgaard strain of "July Elberta."

Dates of first and last picking: June 23 and July 9 (season of 1943).

Tree: Large to medium; vigorous; upright to semi-spreading; open; modified vase formed; hardiness untested; very productive; regular bearer in Southern California.

*Trunk*—Medium stocky; medium smooth.

*Branches*—Medium stocky; medium smooth; glossy. One-year-old growth, side exposed to sun, near Garnet-Brown, oo918, Chart 2, page 192. Side protected from sun, near Lettuce-Green 861/1, Chart 2, page 176. Tender growth, near Pod Green, o61/1, Chart 2, page 120. *Lenticels*—numerous; medium to small.

*Leaves.*—Length—4 to 6 inches. Width—1⅛ to 1⅝ inches. Medium size; lanceolate; acutely pointed; thick to medium; smooth. *Mature leaves*—near Spinach Green, o960/1, Chart 2, page 187. Some of these show a tendency to pucker or wrinkle along midrib. Under side of leaves near Spinach Green, o960/3. *Juvenile leaves*—near Lettuce-Green, 861/1, Chart 2, page 176. *Margin*—glandular; glands somewhat irregularly spaced, and becoming inactive as leaf matures. Serrulate; finely serrate. *Petiole*—medium to short; medium thickness. *Glands*—petiolate. Average number—2 to 5. Opposite; very pronounced; medium large; reniform. Petiolate glands, reniform, near Lettuce-Green, 861, Chart 2, page 176. Position—1 to 3 on petiole and remainder on base of leaf. *Stipules*—These are at an angle about 80° from leaf petiole, ¼ to $\frac{5}{16}$ inch long, margined with stipulate glands, adpressed, and early deciduous.

*Flower-buds.*—Tender; small; short; conic; free.

*Flowers.*—Dates first and full bloom—March 10 and March 17 (season of 1943). In Ontario, California, early to medium compared with other varieties. Small; deep pink (ordinary dictionary significance).

Fruit: Maturity when described—eating ripe June 29th (season of 1943).

*Size.*—Uniform; medium size. Diameter, axial—2¼ to 2¾ inches. Transverse in suture plane—$2\frac{5}{16}$ to 3 inches. At right angles to suture plane—2¼ to 2⅝ inches.

*Form.*—Uniform; some symmetrical, most unsymmetrical; globose. *Suture*—a distinct but fairly shallow line from base to apex, on one side of fruit. Has marked depression beyond pistil point. *Ventral surface*—rounded strongly. No lips or lips indistinct. *Stem cavity*—elongated in suture plane with suture showing on one side. Depth—⅞ to 1 inch. Breadth—⅝ inch. Markings—none distinct. *Base*—oblique. *Apex*—prolonged; rounded. Pistil point—apical to oblique.

*Stem.*—Length—¼ inch; stout; slightly pubescent.

*Adherence to stone.*—Strong.

*Skin.*—Medium thick; tough; free. *Tendency to crack*—none in dry season. *Color*—Color hues at base varying from near Chartreuse-Green, 663/1, Chart 1, page 90, to near Geranium Lake, 20/2, page 20, Chart 1. Darker colors are predominately laid on in flecks and stripes near base. Other portions of skin to apex from near Geranium Lake to near Garnet Brown, oo918/3, Chart 2, page 192. Sometimes fruits are blotched with the Geranium Lake predominating, while others favor patches of Garnet-Brown. When the latter predominates, a purplish hue can be noticed if the fruit is turned toward light. Darker colors are laid on in blotches, stripes and flecks. *Down*—moderate; short; does roll up when rubbed, but only slightly.

*Flesh.*—Near Mimosa Yellow, 602/3, Chart 2, page 143, sometimes varying according to ripeness of fruit, streaked with near Jasper Red, o18/1, Chart 2, page 107. *Surface of pit cavity*—rough, near Chartreuse-Green, 663/1, Chart I, page 90, with markings of varying shades of Pink, deepening in shade as fruit matures.

*Amygdalin.*—Moderate. Juice—abundant; rich.

*Texture.*—Medium firm; fine; melting.

*Fibres.*—Few; fine; tender.

*Ripens.*—Even, usually.

*Flavor.*—Subacid; mild; delicate.

*Aroma.*—Distinct.

*Easting quality.*—Best.

Stone: Free. Adheres to flesh slightly along both dorsal and ventral edges. *Fibres*—short; parts from flesh smoothly.

*Size.*—Medium to small. Length—1¼ inches. Breadth—1 inch. Thickness—$\frac{11}{16}$ to ¾ inch.

*Form.*—Obovate-obovoid; cuneate toward apex.

*Base.*—Oblique. *Hilum*—narrow; oblong. *Apex*—acuminate.

*Sides.*—Equal; sometimes flattened. *Surface*—irregularly furrowed near base and toward apex; pitted toward center.

*Ridges.*—Rounded.

*Pits.*—Some circular; some elongated. *Ventral edge*—thick, with slight wing toward base and apex.

*Dorsal edge.*—Full, with shallow, narrow groove throughout. Ridges on either side—interrupted.

*Color of stone.*—Near Majolica Yellow, o9/3, Chart 2, page 102.

*Tendency to split.*—Slight.

Use: Market; dessert.

Keeping quality: Good.

Resistance: To insects and diseases—only slightly less resistant to delayed dormancy in Southern California than well known "Babcock."

Shipping quality: Good.

I claim:

A new and distinct variety of peach tree, characterized as to novelty by the size of its fruit, with small pit, distinct and unusual coloring of the fruit, the full bodied flavor and excellent balance between sugar and acid, resistance of the plant to delayed dormancy, and its ability to produce regular crops in the Southern California area and to leaf out and to flower and develop high flavor regardless of weather conditions preceding its ripening period, substantially as shown and described.

WALTER E. LAMMERTS.